United States Patent
Ono et al.

(10) Patent No.: US 7,132,230 B2
(45) Date of Patent: Nov. 7, 2006

(54) CYTOTOXIC ASSAY AND NEW ESTABLISHED CELL LINE OF STURGEON ORIGIN

(75) Inventors: Shin-ichi Ono, Shizuoka (JP); Kiyoshi Hiraoka, Ibaraki (JP)

(73) Assignee: Fujikin Incorporated, Osaka (JP)

( * ) Notice: Subject to any disclaimer, the term of this patent is extended or adjusted under 35 U.S.C. 154(b) by 420 days.

(21) Appl. No.: 10/606,803

(22) Filed: Jun. 27, 2003

(65) Prior Publication Data

US 2004/0029102 A1 Feb. 12, 2004

(30) Foreign Application Priority Data

| Jun. 28, 2002 | (JP) | ............................. 2002-189282 |
| Jun. 28, 2002 | (JP) | ............................. 2002-189283 |
| Jun. 4, 2003  | (JP) | ............................. 2003-160007 |

(51) Int. Cl.
*C12Q 1/00* (2006.01)

(52) U.S. Cl. .......................................................... 435/4

(58) Field of Classification Search .................... None
See application file for complete search history.

(56) References Cited

OTHER PUBLICATIONS

Watson et al, "Replication and pathogenesis of white sturgeon iridovirus (WSIV) in experimentally infected white sturgeon Acipenser transmontanus juveniles and sturgeon cell lines" (Diseases of Aquatic Organisms) 1998. vol. 32, pp. 173-184□□.*

Fent, K, "Fish cell lines as versatile tools in ecotoxicology: assessment of cytotoxicity, cytochrome P4501A induction potential and estrogenic activity of chemicals and environmental samples" (Toxicology in Vitro) 2001. Col. 15, pp. 477-488.*

Hiramatsu et al. "Vitellogenin-derived yolk proteins in a hybrid sturgeon, bester: Identification, characterization & course of proteolysis during embryogenesis" (Comparative Biochemistry & Physiology) 2002. vol. 131, pp. 429-441.*

Babich et al. "Fathead Minnow FHM Cells for Use in Vitro Cytotoxicity Assays of Aquatic Pollutants" (Ecotoxicology and Environmental Safety) 1987. Col. 14, pp. 78-87.*

S. Magwood et al., "*In Vitro* Alternatives to Whole Animal Testing. Comparative Cytotoxicity Studies of Divalent Metals in Established Cell Lines Derived From Tropical and Temperate Water Fish Species in a Neutral Red Assay", *Marine Environmental Research* vol. 42, No. 1-4, pp. 37-40, 1996.

H. Babich et al., "*In Vitro* Cytotoxicity Testing of Aquatic Pollutants (Cadmium, Copper, Zinc, Nickel) Using Established Fish Cell Lines", *Ecotoxicology and Environmental Safety* 11, pp. 91-99, 1986.

Ronald P. Hedrick, "Two Cell Lines from White Sturgeon", *Transactions of the American Fisheries Society* 120: 528-534, 1991.

M.F. Li et al., "Fish cell culture: two newly developed cell lines from Atlantic sturgeon (Acipenser oxyrhynchus) and guppy (*Poecilia reticulata*)", *Canadian Journal of Zoology* 63: 2867-2874, 1984.

\* cited by examiner

*Primary Examiner*—Christopher R. Tate
*Assistant Examiner*—Amanda P. Wood
(74) *Attorney, Agent, or Firm*—Armstrong, Kratz, Quintos, Hanson & Brooks, LLP

(57) ABSTRACT

An object of the present invention is to provide a cytotoxic assay using a new established fish cell line. The invention attained according to the object is a cytotoxic assay, wherein an evaluation of toxicity of a specimen is performed on the basis of its toxicity to an established cell line originated from sturgeon, preferably a STIP-1 cell line (FERM BP-8421) and a STIP-3 cell line (FERM BP-8422). Furthermore, another object of the present invention is to provide a new established cell line expected to be used in the diagnosis of viral infection disease of sturgeon and so on. The invention attained according to the object is an established cell line originated from a sturgeon eyeball, particularly a STIP-1 cell line (FERM BP-8421) and a STIP-3 cell line (FERM BP-8422).

14 Claims, 10 Drawing Sheets

Growth curves of STIP-1 cell at respective temperatures

Growth curves of STIP-3 cell at respective temperatures

Influence of fetal bovine serum (FBS) added in L-15 culture medium on the growth of STIP-1 cell Influence of fetal bovine serum (FBS) added in L-15 culture medium on the growth of STIP-3 cell Number of chromosomes of STIP-1 cell Number of chromosomes of STIP-3 cell Chromosome specimen (2n = 173) prepared from STIP-1 cell 74 metacentric centromere types (M-type), 38 sub metacentric centromere types (SM-type), no subterminal centromere type (ST-type), and 61 terminal centromere types.

Chromosome specimen (2n = 126) prepared from STIP-3 cell 64 metacentric centromere types (M-type), 21 sub metacentric centromere types (SM-type), 2 subterminal centromere types (ST-type), and 39 terminal centromere types.

CYTOTOXIC ASSAY AND NEW ESTABLISHED CELL LINE OF STURGEON ORIGIN

BACKGROUND OF THE INVENTION

1. Field of the Invention

The present invention relates to a cytotoxic assay of various kinds of specimens, such as chemical compounds and heavy metals. Furthermore, the present invention relates to a new established cell line expected to be used in the diagnosis of viral infection disease of sturgeon.

2. Background Art

Heretofore the toxicity tests of quality of various specimens such as chemical compounds or heavy metals (zinc, cadmium, copper, arsenic, cobalt, molybdenum, nickel, lead, selenium, chromium, tin, and mercury and so on) have been done with individual animals. However, the method using the individual animals suffers a problem of too much time and expense as well as that from a viewpoint of animal protection. In late years, therefore, toxicity assays that utilize established cell lines (culture cells) (i.e., cytotoxic assays), have been considered.

It is desirable to perform the toxicity test of a specimen in an aqueous environment with an established cell line derived from a fish origin. The toxicity assays using RTG-2 cells which are cells of a fibroblastic established cell line originated from a rainbow trout ovary and FHM cells which are cells of an epithelial established cell line originated from fathead minnow have been considered. However, these methods are not adequate in an aspect of sensitivity. In addition, there is a problem that a growth rate is late and a growth temperature range is small as for the RTG-2 cell, which can not be always satisfactory in an aspect of convenience.

In late years, aquaculture skills continue a remarkable development in increasing the number of fish species which can be cultivated and improving the stabilities in supply. On the other hand, there is a problem of the death of a culture fish by an infection disease caused by, such as bacteria or viruses. In particular, the fact is that there is no measure effective to such a problem even though viral infection disease after leads to a large quantity of deaths. For viral infection disease, it becomes important how early it is checked.

For the diagnosis of viral infection, established cell lines having sensitivities against the virus that is responsible for viral infection in fishes are indispensable. As to the established cell line of fish origin, many established cell lines have been reported since RTG-2 cells which are of a fibroblastic established cell line originated from a rainbow trout ovary were established. However, many of these established cell lines are derived from fibroblastic origins but not epithelial origins. That is, most of them are isolat d, cultured and established from limited fish species such as salmon and carp. Consequently, at present, the diagnosis of viral infection or the isolation of virus itself are not always smoothly performed about a various kinds of fish species.

By the way, sturgeon is the ancient species that has lived for about 300000000 years, but its egg is valued high as caviar, and, also its meat has high utility value as edible, thus it is expected as future culture object fish. In such an aspect, there is an indispensable need for established cell lines to check viral infection disease of sturgeon. However, only a few reports have been published for the established cell lines of sturgeon, although for example, there is a report about the established cell lines of white sturgeon grouped in the genus *Acipenser* in "Transactions of the American Fisheries Society" 120: 528–534, 1991. Therefore, it is very important to establish a new established cell line expected to be used for the diagnosis of viral infection disease of sturgeon. The establishment of such a new established cell line will lead to a great advantage in the production of vaccine effective to viral infection disease of sturgeon and at the time of the cytotoxic tests of chemical compounds, heavy metals or the like.

SUMMARY OF THE INVENTION

Accordingly, it is an object of the present invention to provide a cytotoxic assay using a new established fish cell line. It is another object of the present invention to provide a new established cell line expected to be used in the diagnosis of viral infection disease of sturgeon.

The present invention accomplished in consideration of the above fact, as described in embodiment 1, is a cytotoxic assay, wherein an evaluation of toxicity of a specimen is performed on the basis of its toxicity to an established cell line originated from sturgeon.

In addition, a cytotoxic assay of embodiment 2 is a method using an established cell line of Bester origin.

In addition, a cytotoxic assay of embodiment 3 is a method using an established cell line of an epithelial cell origin.

In addition, a cytotoxic assay of embodiment 4 is a method using an established cell line of an ocular epithelial cell origin.

In addition, a cytotoxic assay of embodiment 5 is a method using an established cell line of an iris pigmented epithelial cell origin.

In addition, a cytotoxic assay of embodiment 6 is a method using an established cell line, where a passage culture of which is possible without adding an extra cellular matrix.

In addition, a cytotoxic assay of embodiment 7 is a method using an established cell line, where 50 times or more of passage cultures of which are possible.

In addition, a cytotoxic assay of embodiment 8 is a method using an established cell line having a doubling time of less than 50 hours on the second day to the sixth day after the initiation of culture at 20° C.

In addition, a cytotoxic assay of embodiment 9 is a method using an established cell line having a plating efficiency of 75% or more, which is the percentage of cells being attached on a culture dish in one hour after adding these cells into the culture dish.

In addition, a cytotoxic assay of embodiment 10 is a method using STIP-1 cells (FERM BP-8421) which are included in an established cell line of a sturgeon eyeball origin.

In addition, a cytotoxic assay of embodiment 11 is a method using STIP-3 cells (FERM BP-8422) which are included in an established cell line of a sturgeon eyeball origin.

In addition, a cytotoxic assay of embodiment 12 is a method using an Alamar Blue assay for the toxic evaluation of a specimen.

In addition, the invention is, as described in embodiment 13, an established cell line of a sturgeon eyeball origin.

In addition, in the established cell line of embodiment 14, sturgeon is Bester.

In addition, the established cell line of embodiment 15 is an ocular epithelial cell origin.

In addition, the established cell line of embodiment 16 is an iris pigmented epithelial cell origin.

In addition, the established cell line of embodiment 17 is an established cell line, where a passage culture of which is possible without adding an extra cellular matrix.

In addition, the established cell line of embodiment 18 is an established cell line, where 50 times or more of passage cultures of which are possible.

In addition, the established cell line of embodiment 19 has a doubling time of less than 50 hours on the second day to the sixth day after the initiation of culture at 20° C.

In addition, the established cell line of embodiment 20 has a plating efficiency of 75% or more, which is the percentage of cells being attached on a culture dish in one hour after adding these cells into the culture dish.

In addition, the established cell line of embodiment 21 is STIP-1 cells (FERM BP-8421) which are included in an established cell line of a sturgeon eyeball origin.

In addition, the established cell line of embodiment 22 is STIP-3 cells (FERM BP-8422) which are included in an established cell line of a sturgeon eyeball origin.

According to the invention, a cytotoxic assay using a new established fish cell line, i.e., an established cell line originated from sturgeon is provided. In addition, according to the present invention, an established cell line originated from a sturgeon eyeball is provided, which can be expected to be used in the diagnosis of viral infection disease of sturgeon and can be of high value even in the production of vaccine effective to viral infection disease of sturgeon and at the time of the cytotoxic tests of chemical compounds, heavy metals, or the like.

DETAILED DESCRIPTION OF THE INVENTION

Figure 1:
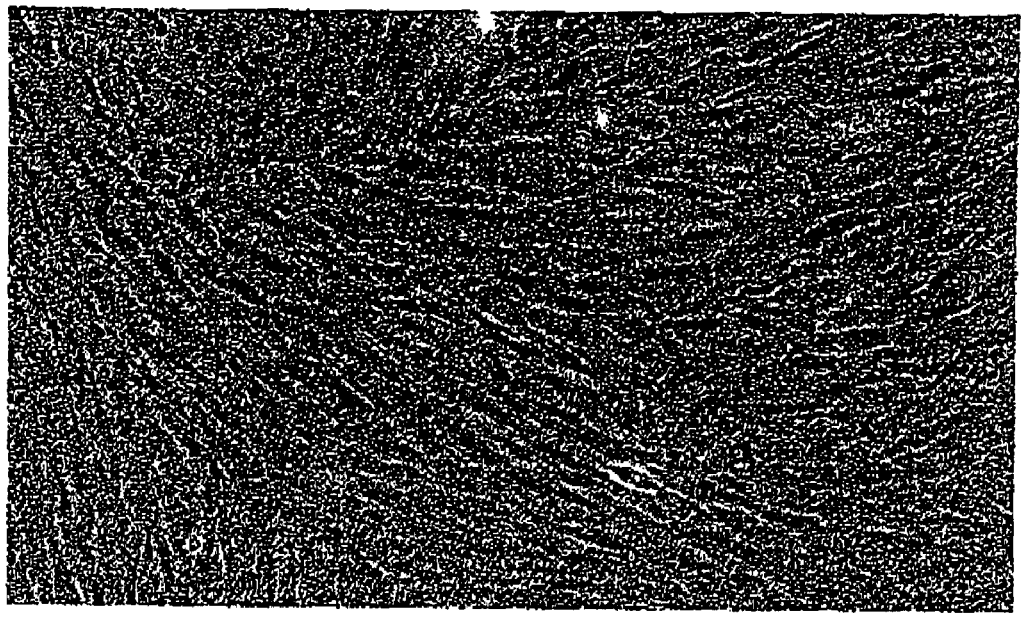
FIG. 1 is a micrograph that represents the STIP-1 cell.

In the cytotoxic assay of the present invention, an established cell line originated from sturgeon is used for evaluating the toxicity of a specimen. Sturgeon may be, for example, one belonging to the genus *Huso* or *Acipenser*, preferably a quality-improved sturgeon, Bester, obtained by cross breeding between a female of Beluga (*H. Huso*) belonging to the genus *Huso* and a male of Sterlet (*A. ruthenus*) belonging to the genus *Acipenser*. As the Bester is a hybrid species, an established cell line originated from Bester has been expected to have both of the characteristics of the genus *Huso* sturgeon's cell and the characteristics of the genus *Acipenser* sturgeon's cell.

For instance, the cell line originated from sturgeon is established from an epithelial cell. The epithelial cell may be one obtained from any part of sturgeon. Preferably, it may be of an epithelial cell of any tissue of an eyeball. A preferable epithelial cell may be an iris pigmented epithelial cell, a retinal pigmented epithelial cell, or the like which is existent without contact with the outer environment. There is no possibility of microbial pollution in these cells originally. Therefore, a microbial contamination of an established cell line is perfectly prevented by aseptically performing a subsequent operation if the cells can be taken out aseptically. The cell line may be stablished from an epithelial cell originated from kidney or ovary. In this case, however, for establishing a cell line, it is necessary to recognize the need of a certain time and labor for only selecting the objective epithelial cell from these tissues for an isolation culture and the undeniable possibility of a microbial contamition.

A method of establishing a cell line may be a well-known method by which primary culture cells are cultured successively. A culture medium may be one prepared by adding fetal bovine serum (FBS) in a Leibovitz's L15 culture medium typically used for culturing fish cells.

A preferable established cell line originated from sturgeon may be, for example, STIP-1 cells (FERM BP-8421) and STIP-3 cells (FERM BP-8422), which are originated from iris pigmented epithelial cells of a Bester eyeball. Each of these cells has higher sensitivity, compared with RTG-2 cells, FHM cells, or the like. In addition, it is superior in an aspect of convenience since each of these cells can be cultured successively without adding an extra cellular matrix and 50 times or more of passage cultures of which can be attained. Among them, the STIP-1 cell has the characteristic features in that a doubling time of less than 50 hours on the second day to the sixth day after the initiation of culture at 20° C., and a plating efficiency of 75% or more, which is the percentage of cells being attached on a culture dish in one hour after adding these cells into the culture dish. Even if a large number of experimental spots are established, therefore, it can be easily and quickly tested.

The toxicity of the specimen to an established cell line originated form sturgeon may be, for example, evaluated using an Alamar Blue assay.

The Alamar Blue assay is one of the bioassay methods being developed to measure the cellular metabolisms of the animal cells or the like. The Alamar Blue pigment is an oxidation-reduction pigment which should be incorporated in a cell for its reduction. The Alamar Blue pigment has the characteristics to be changed from an oxidation type (non-fluorescence/blue) to a reduction type (fluorescence/red) by the reduction reaction of the respiratory metabolism system done in mitochondria. If the cellular metabolism is normal, the reduction reaction proceeds in normal. On the other hand, if the cellular metabolism becomes abnormal, the oxidation type is remained as it is. Therefore, the abnormality of a cellular metabolism can be determined by measuring the change in color. Furthermore, the measurement of a cellular metabolism may be based on the fluorescence and the light absorption. In this case the fluorescence is monitored by an excitation wavelength of 530 nm to 560 nm and a detection wavelength of 590 nm, and the light absorption is monitored at wavelengths of 570 nm and 600 nm.

The Alamar Blue assay is desirable in that the evaluation can be performed easily as the Alamar Blue pigment is water-soluble, and there is no need of extraction and fixation to be required in the bioassay methods using another pigment such as neutral red.

In addition, for example, this Alamar Blue assay can be performed using a commercial kit (manufactured by Biosource Co., Ltd.).

EXAMPLES

Hereinafter, we will describe the present invention more concretely with reference to the following examples.

Example 1

Establishment of a Cell Line Originated from Sturgeon

1. Isolation of iris pigmented Epithelial Cells from a Bester's Eyeball

Eyeballs were extracted from 30 individual Besters of about 15 cm in body length and were then sterilized in 70% ethanol, followed by washing well with PBS (−) added with penicillin and streptomycin. Subsequently, a cornea and a lens were removed from each eyeball and an iris was then cut off. The iris thus obtained was treated with 0.05% EDTA for about 40 minutes to make the separation between the iris pigmented epithelial cell and the connective tissues such as a stroma and a sclera of the iris easily, followed by removing these connective tissues. Isolated iris pigmented epithelial cells in sheet form were subjected to an enzyme treatment with 0.125% trypsin to obtain individually separated cells (primary cells).

2. Primary Culture

The primary cells obtained as described above were seeded in a plastic dish (a culture dish) of 3.5 cm in diameter and cultured using a culture medium prepared by adding 10% fetal bovine serum (FBS) (manufactured by Gibco Co., Ltd.), penicillin (10 unit/ml) and streptomycin (50 μg/ml) in a Leibovitz's L15 culture medium (manufactured by Gibco Co., Ltd.) in a $CO_2$ incubator (air atmosphere) at 20° C. Among the primary cells, cells having excellent growth abilities were selected and then cultured successively.

3. Passage Culture

When the culture dish became confluent with cells, the cells were exfoliated from the culture dish using a solution containing 0.05% EDTA and 0.125% trypsin. Subsequently, the cells were collected by a centrifugal separation and were then transferred to another culture dish, followed by successively culturing the cells using the above culture medium. After repeating a series of these steps, two kinds of cell lines (STIP-1 cells and STIP-3 cells) capable of being cultured for a long time were obtained. These cells are therefore of taxonomy: Animal cell, *Huso huso X Acipenser ruthenus*(Bester). In each of these cell lines to be cultured successively, cells were fixed in the culture dish without the need of coating the bottom surface of the culture dish with an extra cellular matrix such as collagen.

In addition, the above two kinds of the established cell lines were deposited under the Budapest Treaty to National Institute of Advanced Industrial Science and Technology—International Patent Organism Depositary (IPOD), located at AIST Tsukuba Central 6, 1-1 Higashi 1-Chome, Tukuba-shi, Ibaraki-ken, 305-8566 Japan, with the deposition No. FERM BP-8421 for the STIP-1 cells and No. FERM BP-8422 for the STIP-3 cells, respectively. At the time of this patent application, the number of passage cultures of the cell line STIP-1 exceeded 140 times, and the number of passage cultures of the cell line STIP-3 exceeded 80 times, repeatedly.

4. Characteristics of the STIP-1 Cells and the STIP-3 Cells (Form of Cell)

Figure 2:
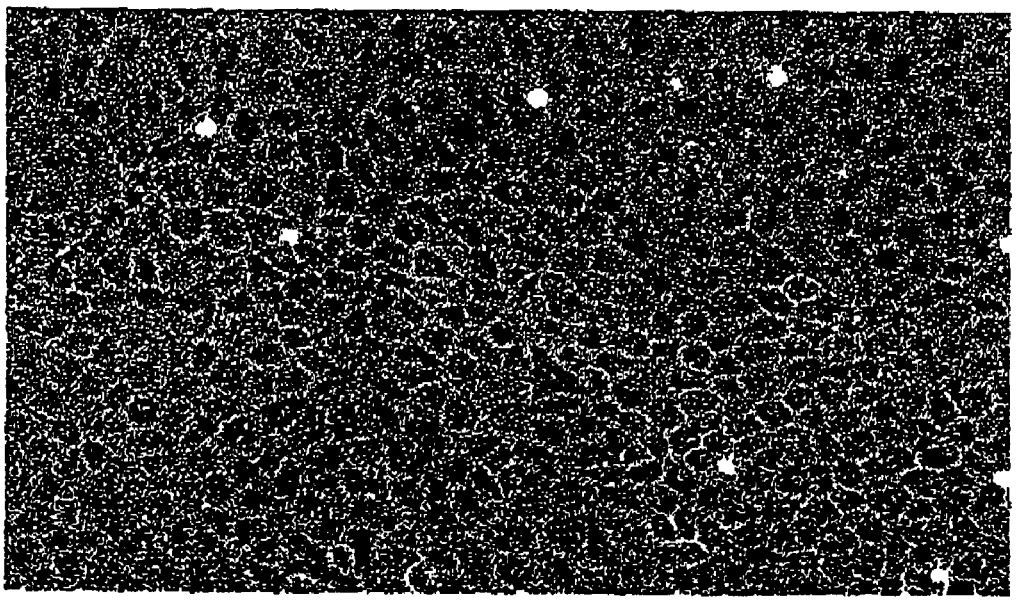
FIG. 2 is a micrograph that represents the STIP-3 cell.

The STIP-1 cells were epithelial cells with elongated shapes (see FIG. 1: A 100-magnification micrograph of cells on the eighth day after the initiation of culture). On the other hand, the STIP-3 cells were typical valvate epithelial cells (see FIG. 2: A 100-magnification micrograph of cells on the fourteenth day after the initiation of culture).

(Temperature Characteristic of Cell)

Figure 3:
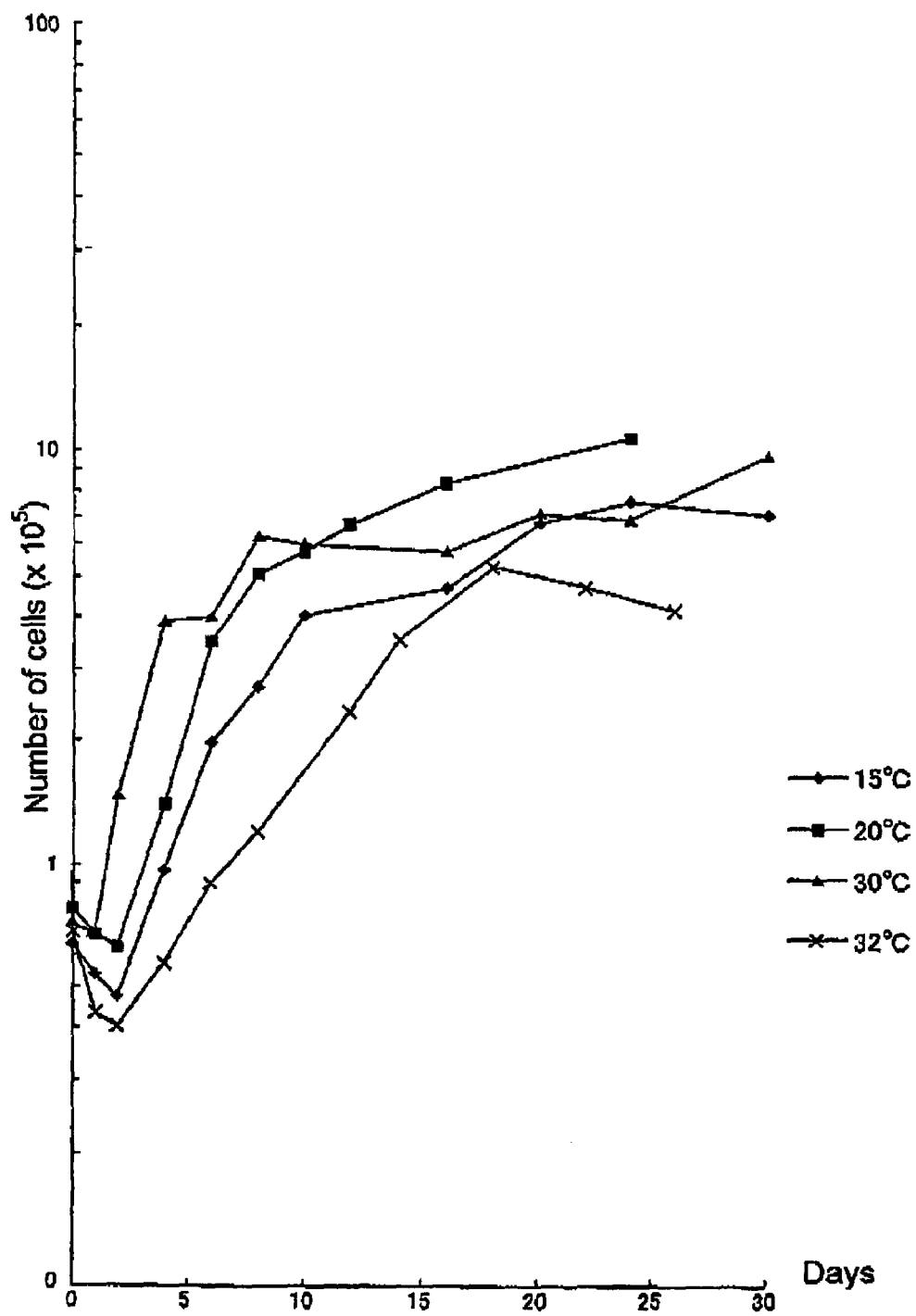
FIG. 3 is a graph that represents the growth curves of the STIP-1 cell at the respective temperatures.
Figure 4:
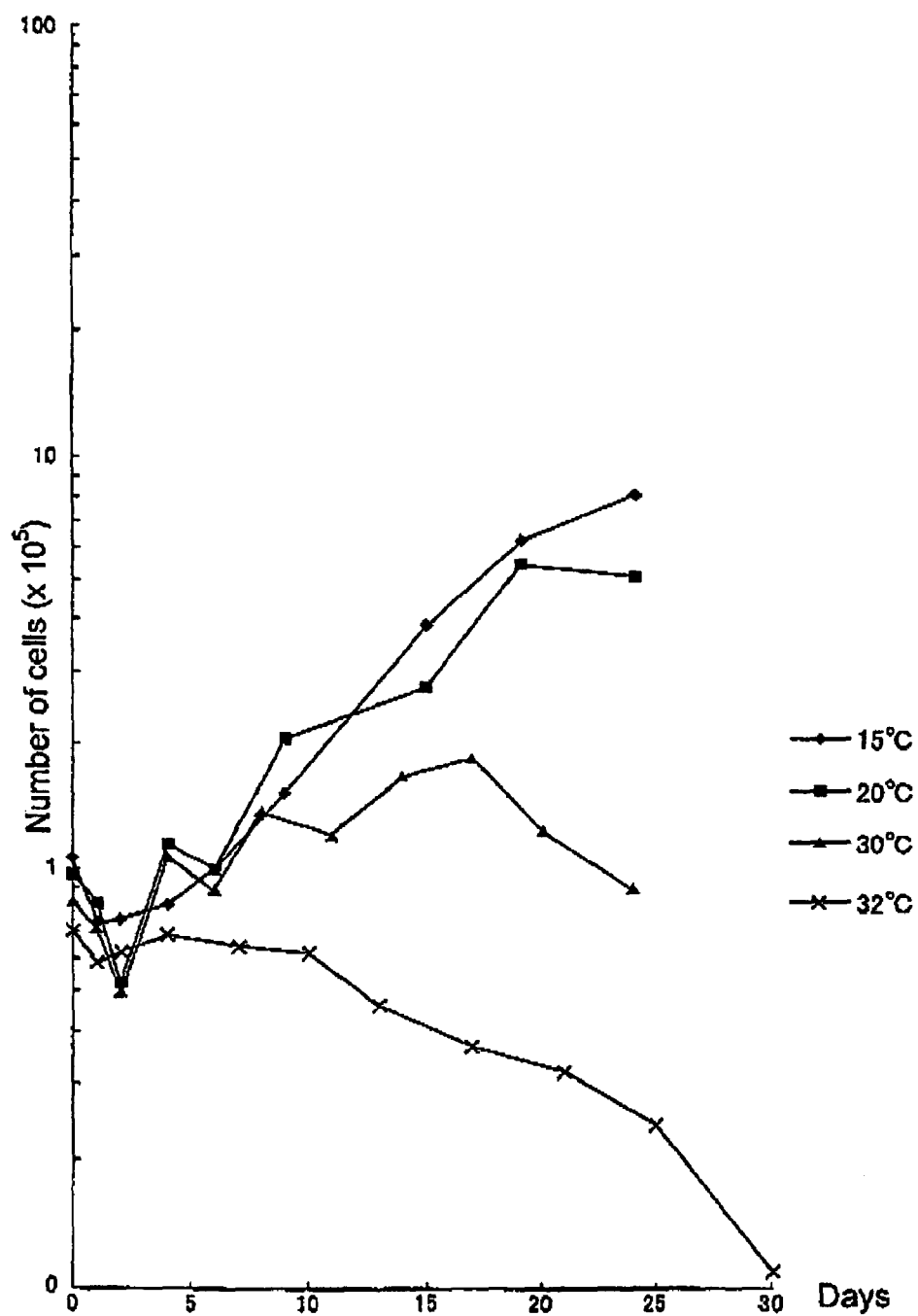
FIG. 4 is a graph that represents the growth curves of the STIP-3 cell at the respective temperatures.

As shown in FIG. 3, the STIP-1 cells indicated good proliferating properties at temperatures in a wide range of 15° C. to 32° C., particularly excellent at 20° C. A doubling time of the cells on the second day to the sixth day after the initiation of culture at 20° C. (the time that cells multiply exponentially) was 38.9 hours, resulting in a growth rate thereof about two times higher than the RTG-2 cells. On the other hand, as shown in FIG. 4, the STIP-3 cells indicated good proliferating properties at temperatures ranging from 15° C. to 20° C. If the temperature is 30° C. or more, the proliferating properties of the STIP-3 cells were inhibited. A doubling time of the cells on the second day to the sixth day after the initiation of culture at 20° C. was 74.9 hours.

(Influence of FBS on the Cell Growth)

Figure 5:
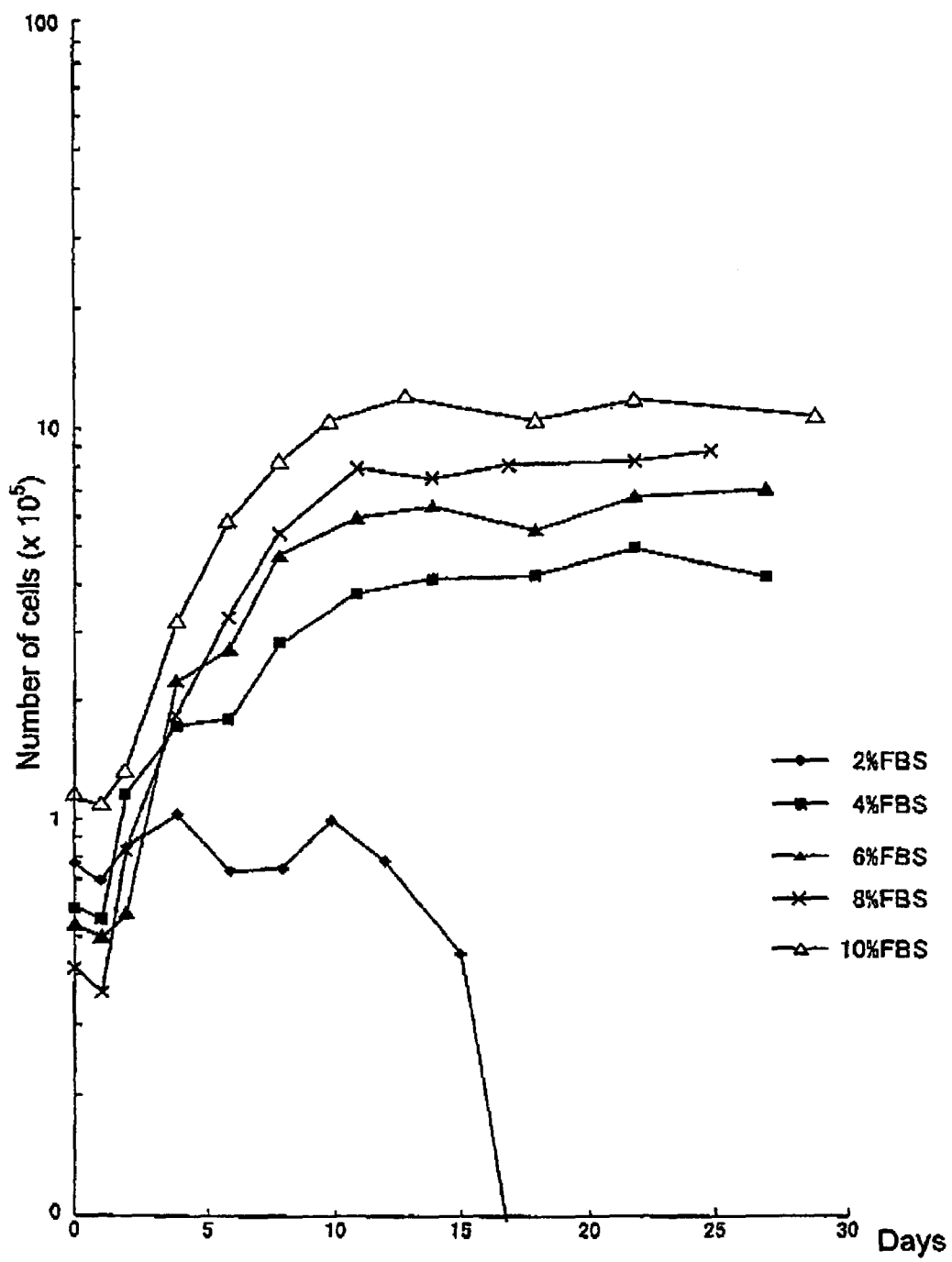
FIG. 5 is a graph that illustrates the influence of FBS on the growth of the STIP-1 cell.
Figure 6:
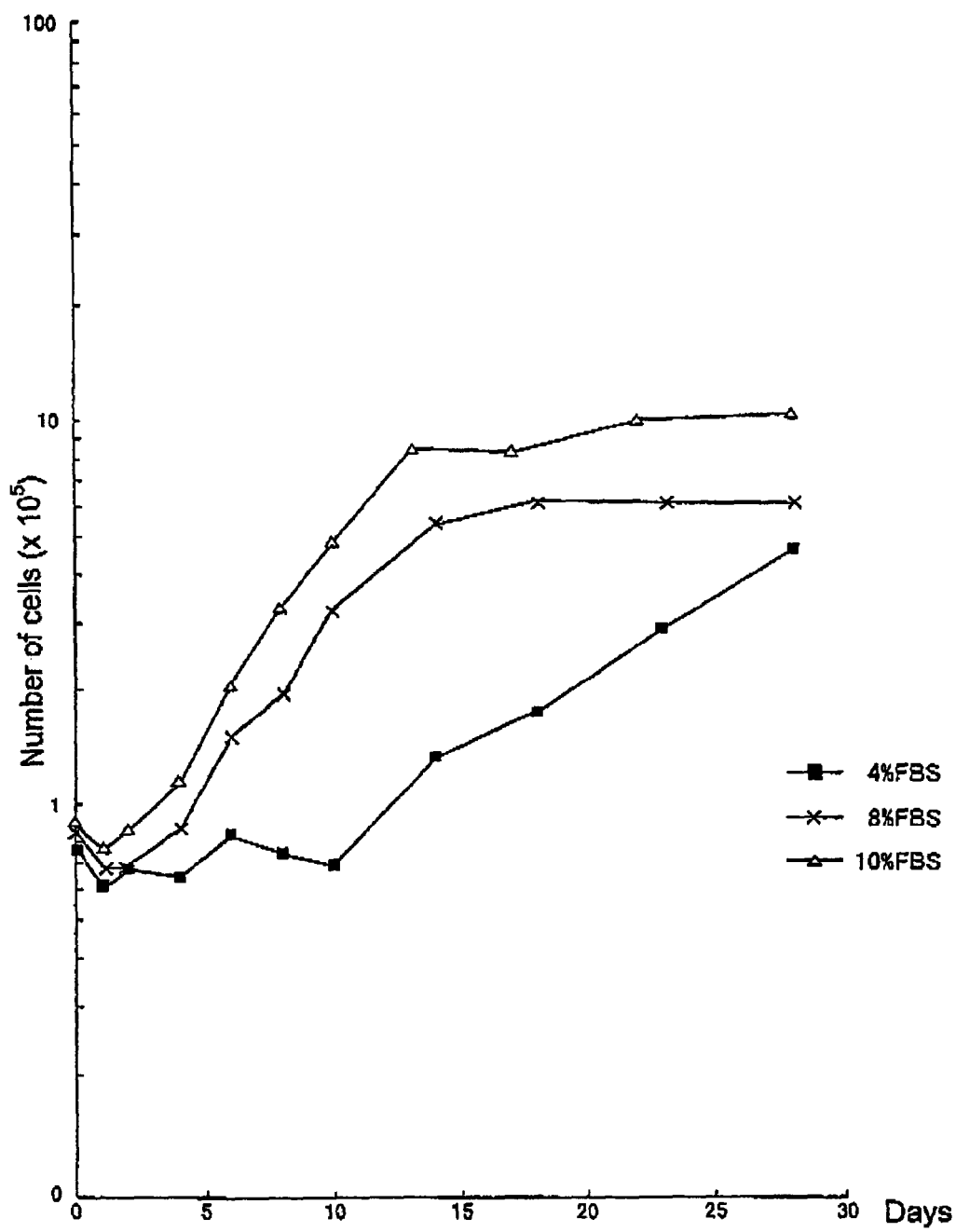
FIG. 6 is a graph that illustrates the influence of FBS on the growth of the STIP-3 cell.

As shown in FIG. 5, a sufficient concentration of FBS to be added in the Leibovitz's L15 culture medium required for the proliferation of the STIP-1 cells was 4%. In addition, as shown in FIG. 6, a sufficient concentration of FBS to be added in the Leibovitz's L15 culture medium required for the proliferation of the STIP-3 cells was 4%. Accordingly, since FBS required for the proliferation of these cell lines was small, it was found that a mass culture of each of these cell lines was economically effective.

(Number of Chromosome in Cell)

Figure 7:
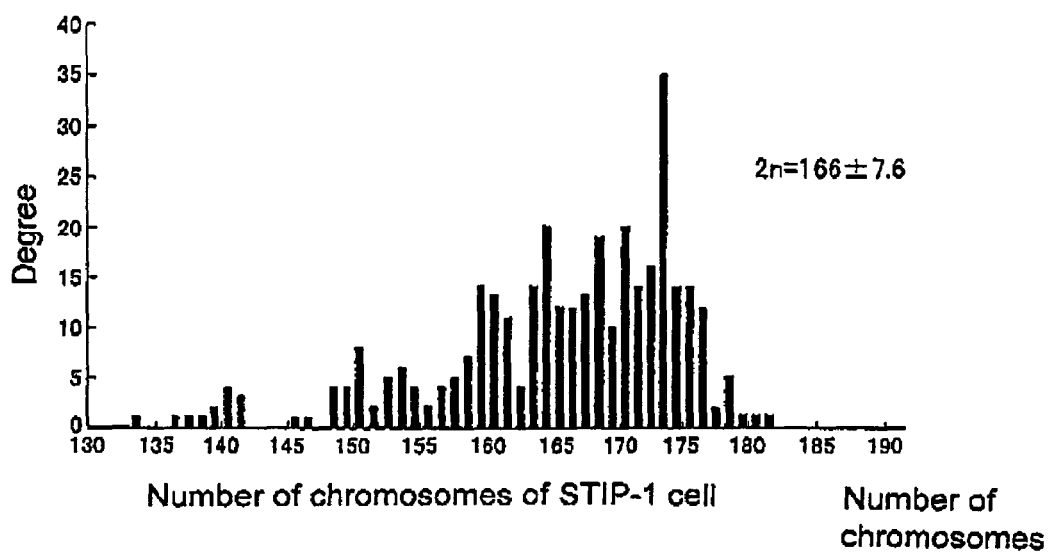
FIG. 7 is a graph that represents the number of chromosomes of each of the STIP-1 cell and the STIP-3 cell.
Figure 7:
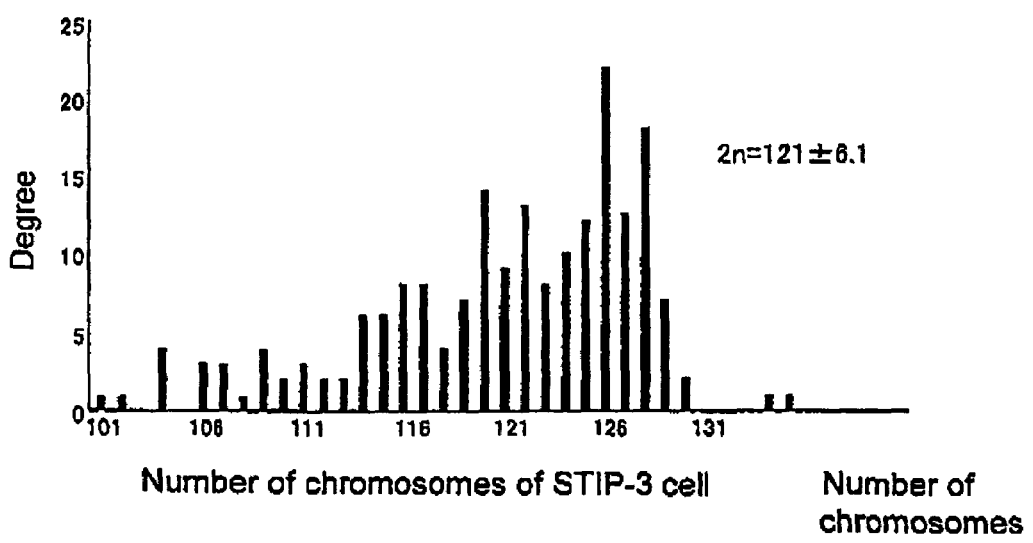
Figure 8:
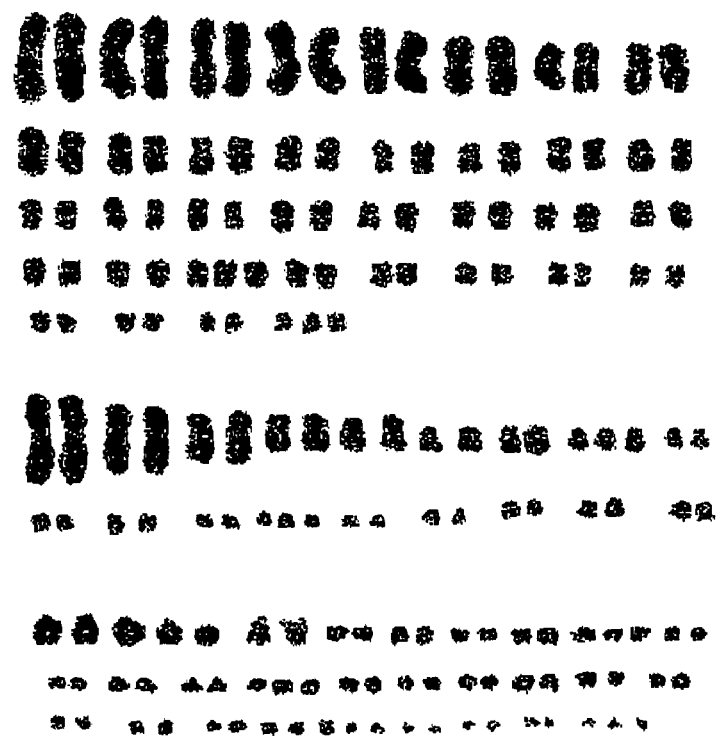
FIG. 8 is a diagram that represents the STIP-1 cell's chromosomal specimen.
Figure 9:
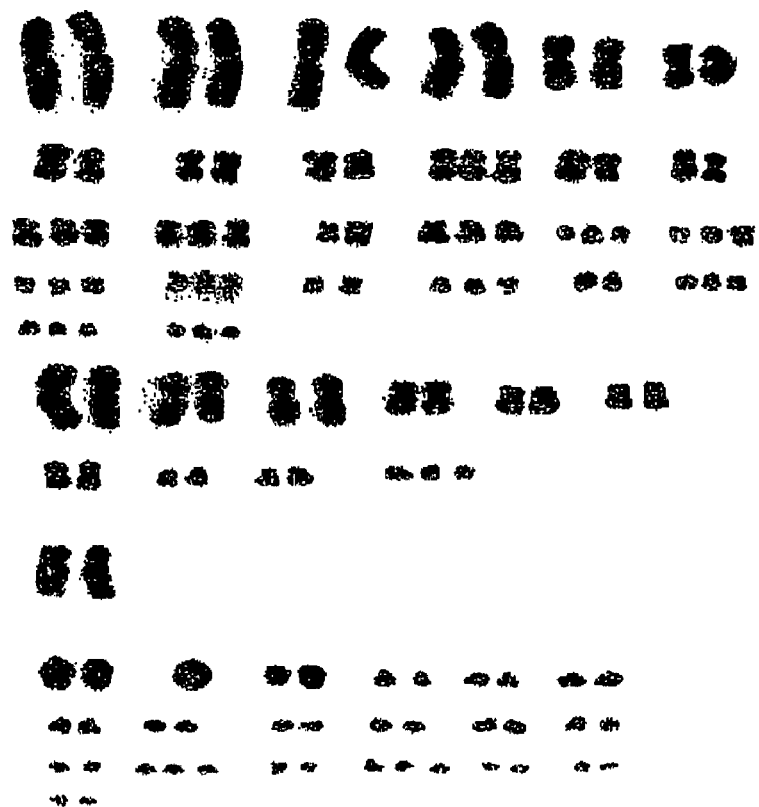
FIG. 9 is a diagram that represents the STIP-3 cell's chromosomal specimen.

The number of chromosomes of the STIP-1 cells and the number of chromosomes of the STIP-3 cells were examined by the conventional procedures in which a colchicine treatment was performed on the logarithmic-growth cells on the sixth day after the initiation of culture, which cells were at the time of 80 times of passage cultures. Concretely, the colchicine was added to the cells so that the final concentration thereof became 0.20 μg/ml. After culturing for 18 hours, the culture medium was removed and the cells were washed with PBS (−). Subsequently, the cells were exfoliated from the culture dish using a solution containing 0.05% EDTA and 0.125% trypsin, and were then collected by a centrifugal separation. The cells being collected was added with 0.075M of KCl, followed by being placed for 20 minutes at room temperature in a hypotonic treatment. The hypotonic-treated cellular suspension was fixed with a Carnoy fluid in ice for 20 minutes and was then provided a chromosome specimen by a frame dry method. Subsequently, a Giemsa staining was performed on the chromosome specimen and the number of chromosomes was counted under a microscopic observation (a magnification of 1000 times) As a result, the number of chromosomes, of the STIP-1 cells was 2n=166±7.6, and the number of chromosomes of the STIP-3 cells was 2n=121±6.1. In each cell line, the number of chromosomes was increased, compared with the number of chromosomes of Bester (2n=117) (see FIG. 7). It is characterized by this result that both cells are established cell lines. When the chromosome was classified, both cells were basically diploids, but aneuploid was shown at random. An example of the chromosome specimen of the STIP-1 cell having 2n=173 is shown in FIG. 8, and an example of the chromosome specimen of the STIP-3 cell having 2n=126 is shown in FIG. 9.

(Adhesive Property of Cell)

Figure 10:
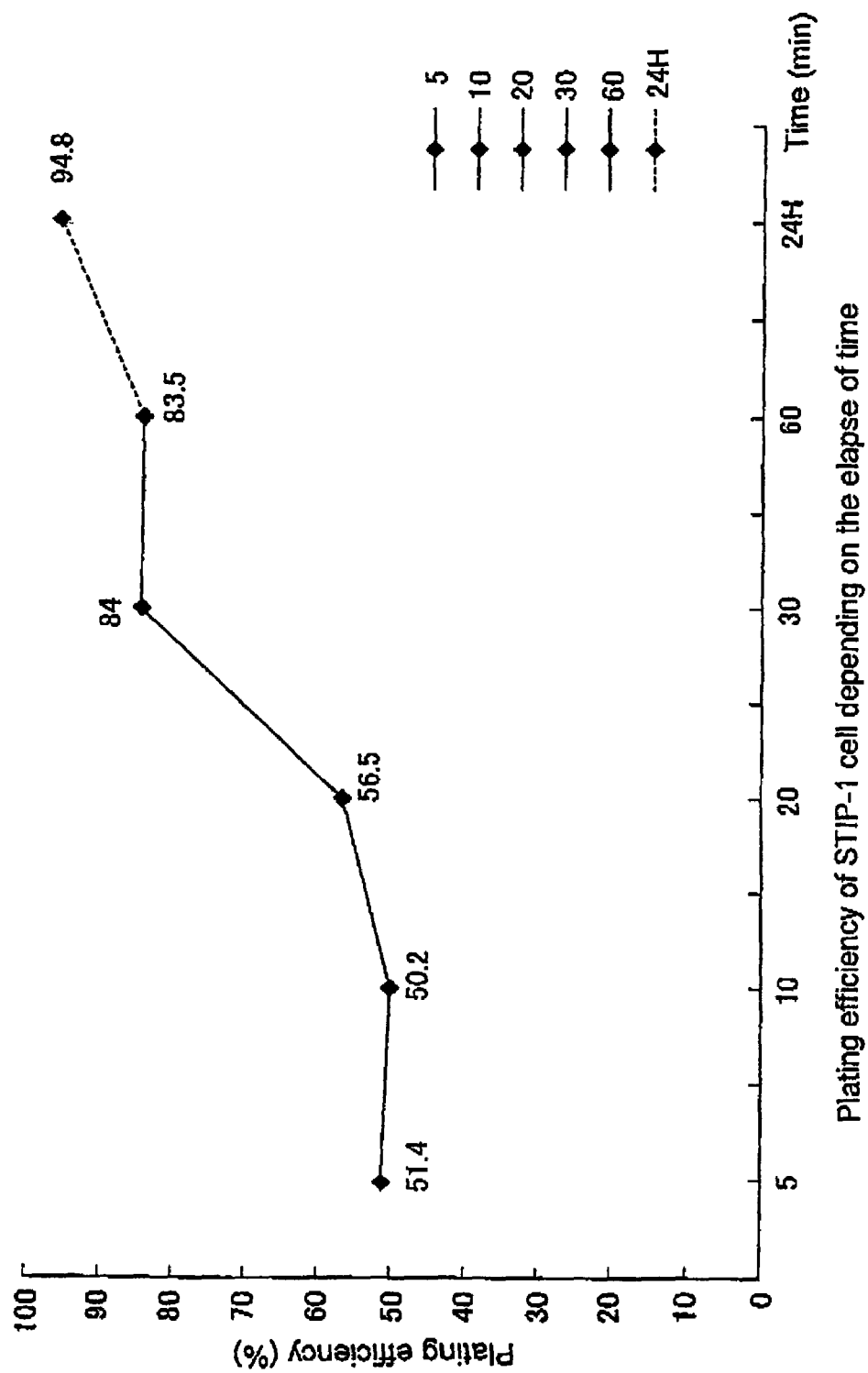
FIG. 10 is a graph that represents the adhesion properties of the STIP-1 cell to the culture dish.

The adhesive properties of the STIP-1 cells on the culture dish were investigated with reference to the time period from the addition of cells to the culture dish to the adhesion of cells thereon (Plating efficiency: a percentage expression of a value obtained by dividing the number of cells fixed on the culture dish after a predetermined time with the total cell number added to the culture dish). The results are shown in FIG. 10. As is evident from FIG. 10, the STIP-1 cells showed a plating efficiency of 51.4% after 5 minutes from the addition of cells to the culture dish. They showed a plating efficiency of 83.5% after one hour, and an extremely high plating efficiency of 94.8% after 24 hours.

Example 2

Cytotoxic Test of Heavy Metals Using the STIP-1 Cells and the STIP-3 Cells (A) Cytotoxicities of Cadmium to the STIP-1 Cells and the STIP-3 Cells were Evaluated as Follows.

1. Method

Cells were cultured in a 96-well microtiter plate in a $CO_2$ incubator (air atmosphere) at 20° C. until it became confluent. The culture was performed using a culture medium prepared by adding 10% fetal bovine serum (FBS) (manufactured by Gibco Co., Ltd.), penicillin (10 unit/ml) and streptomycin (50 μg/ml) in a Leibovitz's L15 culture medium (manufactured by Gibco Co., Ltd.).

A 0.2M aqueous solution of a specimen (cadmium chloride, $CdCl_2.2H_2O$) was prepared and was then sterilized by passing through a filter of 0.2 μm in pore size to be preserved at 4° C. From this cadmium aqueous solution, cadmium aqueous solutions having 9 different concentrations of 0.01 mM, 0.025 mM, 0.05 mM, 0.075 mM, 0.1 mM, 0.25 mM, 0.5 mM, 0.75 mM, and 1 mM, respectively were prepared and inoculated in the respective wells. For a comparison example, the culture medium in the absence of the specimen was inoculated in a well. After 24 hours passed, an Alamar Blue pigment was added and an additional culture was continued for further 24 hours.

Subsequently, by using a microplate reader, the light absorbance of each well was measured using two wavelengths (570 nm and 600 nm). The inhibition value of a cellular metabolism with the cadmium aqueous solution was measured as a reduction rate of a well (a sample) inoculated with a cadmium aqueous solution to a well only containing the culture medium as a control The calculation was performed using the following equation.

Inhibition value (%)=100−(A/B)×100

* A=sample well (A570 nm−A600 nm)−blank well (A570 nm−A600 nm), and

B=control well (A570 nm−A600 nm)−blank well (A570 nm−A600 nm).

In addition, (A/B)×100 means a survival rate (%) of cells.

In the above method, the evaluation of the toxicity of cadmium to each of the STIP-1 cells and the STIP-3 cells was performed on the basis of a toxicity concentration value $EC_{50}$ which effects on 50% of the cells.

2. Results

Figure 11:
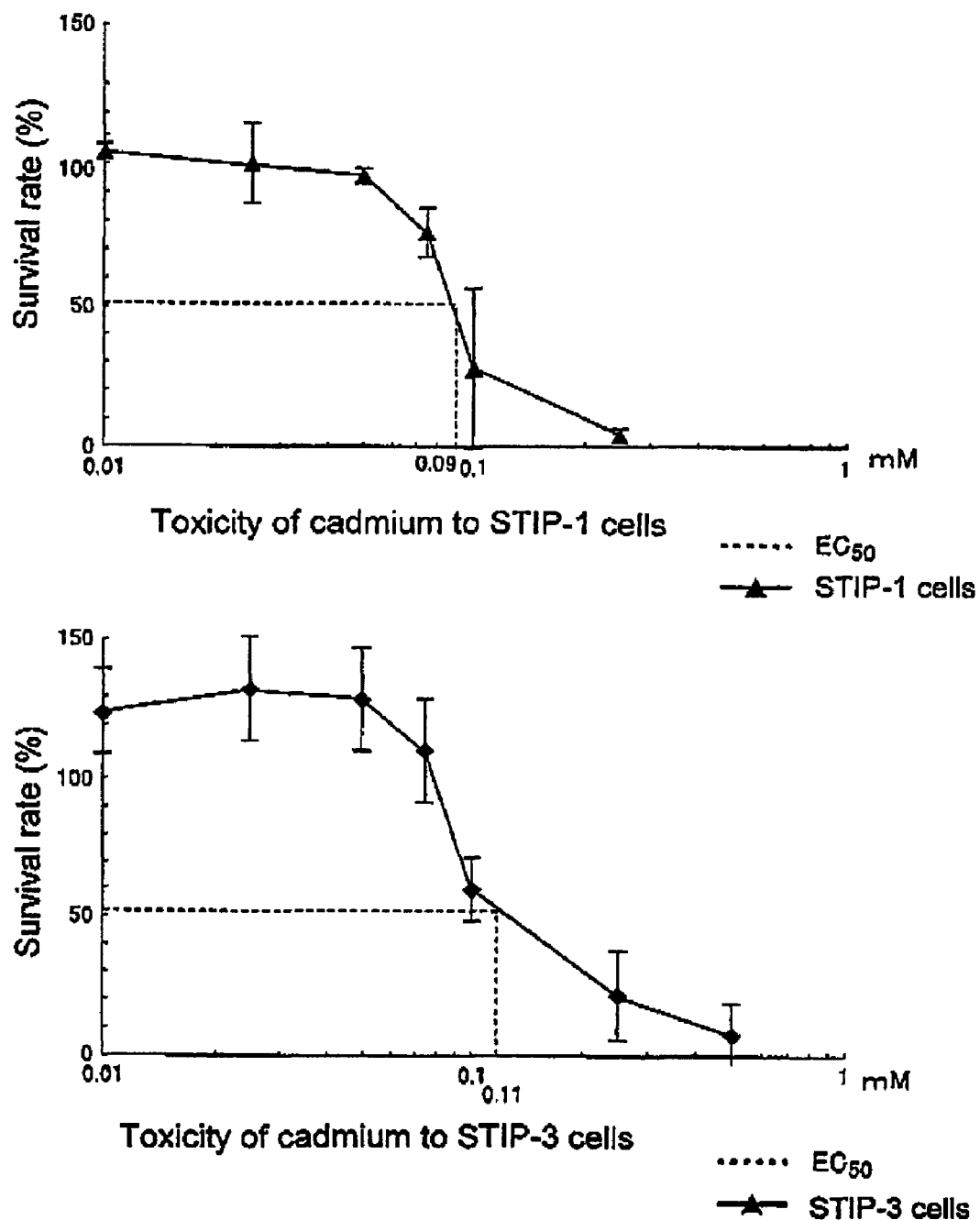
FIG. 11 is a graph that represents the toxicities of cadmium to the STIP-1 cell and the STIP-3 cell.

The $EC_{50}$ value of cadmium to the STIP-1 cells was 0.089 mM, and the $EC_{50}$ value of cadmium to the STIP-3 cells was 0.1 mM (see FIG. 11). These $EC_{50}$ values were smaller than the $EC_{50}$ value obtained from the RTG-2 cells or the FHM cells, 0.18 mM to 0.38 mM. It revealed that the STIP-1 cells and the STIP-3 cells had excellent sensitivities higher than those of the RTG-2 cells and the FHM cells, respectively.

(B) Evaluations of toxicities of eight kinds of heavy metals except of cadmium to the STIP-1 cells were performed by the same way as described in the above (A). The results were shown in Table 1.

TABLE 1

| Heavy Metals | $EC_{50}$ (mM) |
|---|---|
| $CoCl_2.6H_2O$ | 2.2000 |
| $CuCl_2.2H_2O$ | 1.3200 |
| $HgCl_2$ | 0.0850 |
| $MnCl_2.4H_2O$ | 0.4000 |
| $NiCl_2.6H_2O$ | >10 |
| $Pb(NO_3)_2$ | 3.3000 |
| $ZnSO_4.7H_2O$ | 0.4000 |
| Tributyl tin | 0.0009 |

(C) Summary of the Example 2

As a result of performing the evaluations of the toxicities of nine kinds of heavy metals to the STIP-1 cells, tributyl tin showed the strongest toxicity, and the $EC_{50}$ value thereof was $9 \times 10^{-4}$ mM. Tributyl tin showed its toxicity at a concentration about 100 times lower than other heavy metals. Furthermore, heavy metals that showed toxicities to the STIP-1 cells can be arranged in toxic strong order: tin>mercury>cadmium>zinc=manganese>copper>cobalt >lead>nickel. It was the same tendency as the toxicities to the culture cells of other fish origins previously reported. Among them, manganese showed the strong toxicity to the STIP-1 cells about 10 times more than that to the culture cells of other fish origins.

Example 3

Cytotoxic Test of Phenols Using the STIP-1 Cells

Evaluations of toxicities of twelve kinds of phenols to the STIP-1 cells were performed by the same way as described in Example 2 (A). The results were shown in Table 2.

TABLE 2

| Phenols | $EC_{50}$ (mM) |
|---|---|
| Phenol | 8.6000 |
| p-nitrophenol | 0.3500 |
| p-chlorophenol | 0.8000 |
| 2,3-dichlorophenol | 0.0800 |
| 2,4-dichlorophenol | 0.0550 |
| 2,5-dichlorophenol | 0.0560 |
| 2,6-dichlorophenol | 0.9000 |
| 3,4-dichlorophenol | 0.0300 |
| 2,4,5-trichlorophenol | 0.0070 |
| 2,4,6-trichlorophenol | 0.7000 |
| 2,3,4,6-tetrachlorophenol | 0.0090 |
| Pentachlorophenol | 0.0900 |

As is evident from Table 2, 2,4,5-trichlorophenol showed the strongest toxicity to the STIP-1 cells. The $EC_{50}$ values of twelve kinds of phenols investigated this time were two to six times lower than the $EC_{50}$ values to the culture cells of other fish origins. It indicated that the STIP-1 cells were useful cells for investigating the toxicities of phenols.

What is claimed is:

1. The cytotoxic assay comprising contacting a test specimen with an established cell line originated from sturgeon eyeball, and evaluating the toxicity of the specimen to said cell line.

2. The cytotoxic assay as claimed in claim 1, wherein said established cell line is of Bester origin.

3. The cytotoxic assay as claimed in claim 1, wherein said established cell line is of an epithelial cell origin.

4. The cytotoxic assay as claimed in claim 3, wherein said established cell line is of an ocular epithelial cell origin.

5. The cytotoxic assay as claimed in claim 4, wherein said established cell line is of an iris pigmented epithelial cell origin.

6. The cytotoxic assay as claimed in claim 1, wherein said established cell line is a cell line where a passage culture of which is possible without adding an extra cellular matrix.

7. The cytotoxic assay as claimed in claim 1, wherein said established cell line is a cell line where 50 times or more of passage cultures of which are possible.

8. The cytotoxic assay as claimed in claim 1, wherein said established cell line has a doubling time of less than 50 hours on the second day to the sixth day after the initiation of culture at 20° C.

9. The cytotoxic assay as claimed in claim 1, wherein said established cell line has a plating efficiency of 75% or more, which is the percentage of cells being attached on a culture dish in one hour after adding these cells into the culture dish.

10. The cytotoxic assay as claimed in claim 1, wherein said established cell line is STIP-1 cells (FERM BP-8421), which are of a sturgeon eyeball origin.

11. The cytotoxic assay as claimed in claim 1, wherein said established cell line is STIP-3 cells (FERM BP-8422), which are of a sturgeon eyeball origin.

12. The cytotoxic assay as claimed in claim 1, wherein the cytotoxic assay is an Alamar Blue assay for the toxic evaluation of said specimen.

13. The cytotoxic assay as claimed in claim 1, wherein said specimen is selected from the group consisting of chemical compounds and heavy metals.

14. The cytotoxic assay as claimed in claim 13, wherein said heavy metals are selected from the group consisting of zinc, cadmium, copper, arsenic, cobalt, molybdenum, nickel, lead, selenium, chromium, tin, and mercury.

* * * * *